United States Patent
Yamamoto et al.

(10) Patent No.: US 8,123,520 B2
(45) Date of Patent: Feb. 28, 2012

(54) ORTHODONTIC APPLIANCE WITH VIBRATION GENERATION

(75) Inventors: Teruko Yamamoto, Okayama (JP); Hiroshi Kamioka, Kurashiki (JP); Taiji Adachi, Kyoto (JP); Shogo Fukushima, Moriguchi (JP); Takumi Sakimura, Osaka (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 173 days.

(21) Appl. No.: 11/813,375

(22) PCT Filed: Apr. 12, 2007

(86) PCT No.: PCT/JP2007/058043
§ 371 (c)(1),
(2), (4) Date: Jul. 5, 2007

(87) PCT Pub. No.: WO2008/065761
PCT Pub. Date: Jun. 5, 2008

(65) Prior Publication Data
US 2009/0042159 A1     Feb. 12, 2009

(30) Foreign Application Priority Data
Nov. 27, 2006 (JP) .................. 2006-318007

(51) Int. Cl.
*A61C 3/00* (2006.01)
(52) U.S. Cl. ........................................ 433/18
(58) Field of Classification Search .............. 433/18–21, 433/37, 41–48, 24; 601/46, 48, 70, 72, 73, 601/78, 80, 97, 101, 108, 110
See application file for complete search history.

(56) References Cited

U.S. PATENT DOCUMENTS

| | | | | |
|---|---|---|---|---|
| 3,332,150 A | * | 7/1967 | Mumaw | 433/24 |
| 4,123,844 A | * | 11/1978 | Kurz | 433/5 |
| 4,229,165 A | | 10/1980 | Kurz | |
| 4,244,688 A | | 1/1981 | Kurz | |
| 4,348,177 A | | 9/1982 | Kurz | |
| 4,348,178 A | | 9/1982 | Kurz | |

(Continued)

FOREIGN PATENT DOCUMENTS

DE         4020647         1/1992

(Continued)

OTHER PUBLICATIONS

English language Abstract of JP 2002-102255, Apr. 9, 2002.

(Continued)

*Primary Examiner* — Todd Manahan
*Assistant Examiner* — Matthew Nelson
(74) *Attorney, Agent, or Firm* — Greenblum & Bernstein P.L.C.

(57) ABSTRACT

The present invention aims to provide an orthodontic appliance capable of efficiently applying vibration to teeth to be aligned and enabling a treatment to be easily and safely continued even at home. This appliance is provided with a load applying mechanism and a vibration generating actuator. The load applying mechanism is mounted on teeth to apply a load for the malocclusion correction to a specified tooth in the teeth. The vibration generating actuator includes a contact portion that is inserted into a buccal cavity containing the teeth and can come into contact with a part of the load applying mechanism corresponding to the specified tooth or the specified tooth, and applies a vibration force from the contact portion to the specified tooth or the part of the load applying mechanism.

9 Claims, 7 Drawing Sheets

U.S. PATENT DOCUMENTS

| | | | |
|---|---|---|---|
| 4,382,780 A * | 5/1983 | Kurz | 433/5 |
| 4,511,330 A | 4/1985 | Smiley et al. | |
| 5,106,302 A * | 4/1992 | Farzin-Nia et al. | 433/215 |
| 5,334,015 A | 8/1994 | Blechman | |
| 5,967,784 A | 10/1999 | Powers | |
| 5,975,893 A | 11/1999 | Chishti et al. | |
| 6,183,248 B1 | 2/2001 | Chishti et al. | |
| 6,210,162 B1 | 4/2001 | Chishti et al. | |
| 6,217,325 B1 | 4/2001 | Chishti et al. | |
| 6,227,850 B1 | 5/2001 | Chishti et al. | |
| 6,227,851 B1 | 5/2001 | Chishti et al. | |
| 6,299,440 B1 | 10/2001 | Phan et al. | |
| 6,309,215 B1 | 10/2001 | Phan et al. | |
| 6,390,812 B1 | 5/2002 | Chishti et al. | |
| 6,471,511 B1 | 10/2002 | Chishti et al. | |
| 6,633,747 B1 | 10/2003 | Reiss | |
| 7,163,399 B2 | 1/2007 | Kajimoto et al. | |
| 2002/0051951 A1* | 5/2002 | Chishti et al. | 433/6 |
| 2004/0013993 A1 | 1/2004 | Ito | |
| 2004/0058295 A1 | 3/2004 | Bergersen | |
| 2004/0209218 A1 | 10/2004 | Chishti et al. | |
| 2007/0065768 A1 | 3/2007 | Nadav | |

FOREIGN PATENT DOCUMENTS

| | | |
|---|---|---|
| JP | 4-46585 | 7/1992 |
| JP | 11-155273 | 6/1999 |
| JP | 2001-340412 | 12/2001 |
| JP | 2002-102255 | 4/2002 |
| JP | 2003-290250 | 10/2003 |
| JP | 2004-113625 | 4/2004 |
| JP | 2004-201895 | 7/2004 |
| WO | 00/19928 | 4/2000 |
| WO | 02/073185 | 9/2002 |
| WO | 2005/092234 | 10/2005 |

OTHER PUBLICATIONS

English language Abstract of JP 2004-201895, Jul. 22, 2007.
English language Abstract of JP 2003-290250, Oct. 14, 2003.
English language Abstract of JP 2001-340412, Dec. 11, 2001.
English language Abstract of JP 2004-113625, Apr. 15, 2004.
English language Abstract of JP 11-155273, Jun. 8, 1999.
Shimizu, "A study of the movement of the lateral incisor of the macaca fuscata loaded by a vibrating force," Journal of Japan Orthodontic Society, 45, pp. 56-72, 1986 (including an English language Abstract).
Ohmae et al., "Biomechanical acceleration of experimental tooth movement by ultrasonic vibration in vivo: Part 1, Homo-directional application of ultrasonication to orthodontic force," Journal of Japan Orthodontic Society, Orthod. Wave, 60(4), pp. 201-212, 2001 (including an English language Abstract).
Chiba et al., "Effects of Mechanical stimulation using resonance vibration on the periodontium" (including an English language Abstract), Am J Orthod Dentofacial Orthop 2008.
Emata, "The mechanical response of the periodontal structure in the maxillary lateral incisor of the macaca fuscata yakui, loading by a vibrating force," Japanese Journal of Oral Bial., 21:571-585, 1979 (including an English language Abstract).
U.S. Appl. No. 11/721,085 to Yamamoto et al., filed Jun. 7, 2007.
U.S. Appl. No. 11/721,086 to Yamamoto et al., filed Jun. 7, 2007.
U.S. Appl. No. 11/721,129 to Yamamoto et al., filed Jun. 7, 2007.
Search report from E.P.O., mail date is Feb. 15, 2011.

* cited by examiner

ORTHODONTIC APPLIANCE WITH VIBRATION GENERATION

TECHNICAL FIELD

The present invention relates to an orthodontic appliance.

BACKGROUND ART

An orthodontic appliance equipped with an orthodontic wire to be mounted on teeth has been conventionally known. An elastic restoring force of the orthodontic wire acts as a constant static load on the teeth to correct teeth malalignment or crossbite. In other words, the orthodontic appliance is based on the principle of aligning the teeth by gradually deforming an alveolar bone supporting the teeth in the gum (bone reconstruction, bone remodeling) through the application of a constant force to the teeth.

However, the teeth alignment using the orthodontic wire takes a very long time (fastest six months, normally several years) until an orthodontic treatment is finished. Such a long treatment period increases burdens on patients, causing them to give up easily.

Figure 7A:
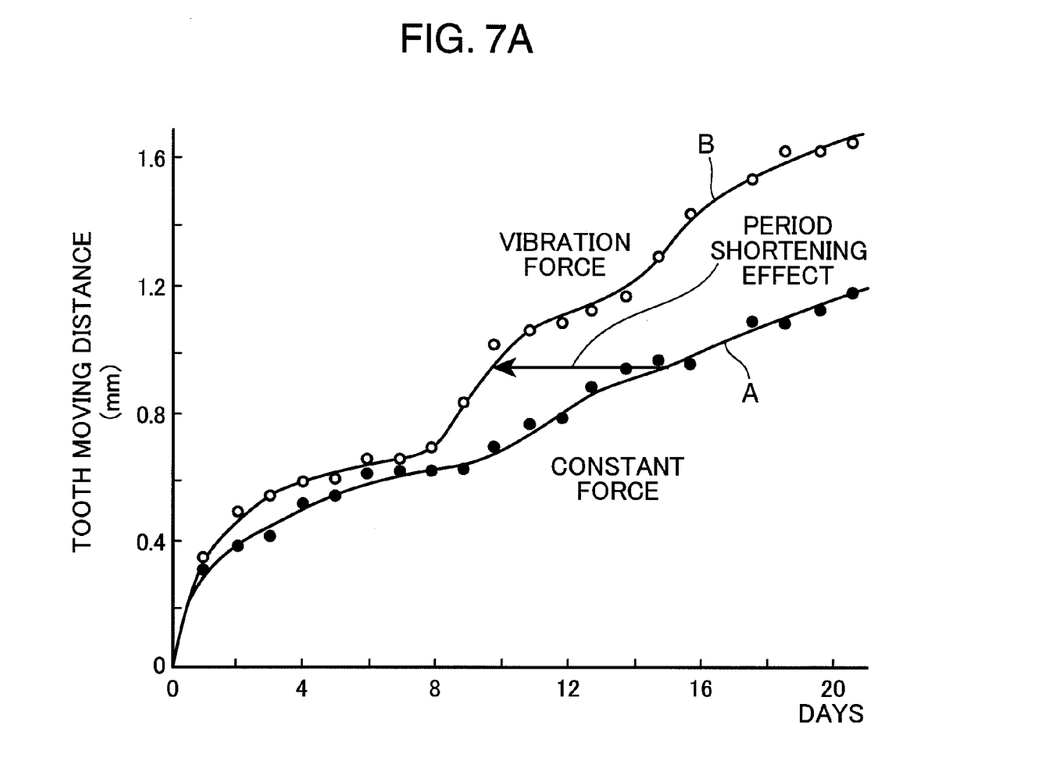
FIGS. 7A and 7B are graphs respectively showing an effect of shortening a period of orthodontic treatment.
Figure 7B:
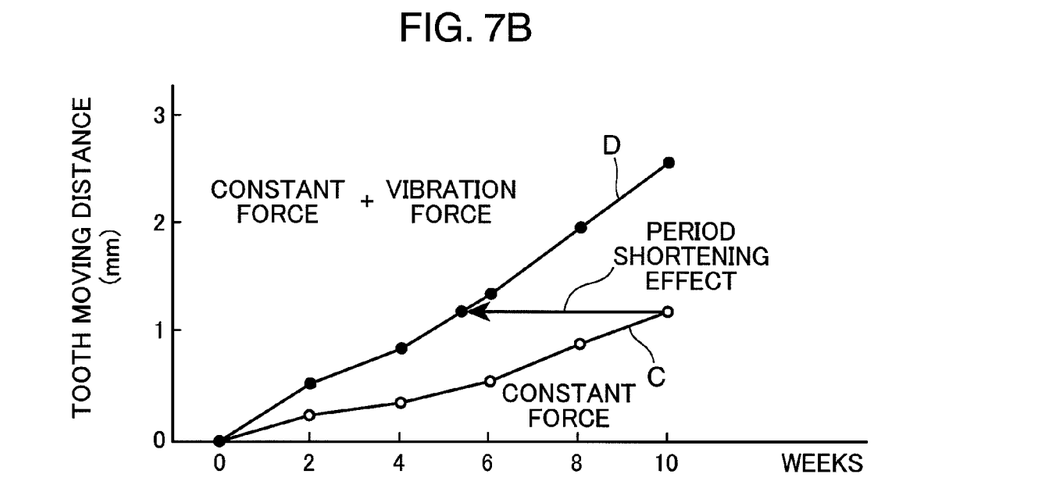

In order to shorten a period of such an orthodontic treatment, technology of giving a vibration force to the teeth has been studied. For example, a study result to the effect that if a sample A in which a constant force was applied to the teeth and a sample B in which a vibration force was applied to the teeth are compared, the sample B in which the vibration force was applied is more effective in shortening the period as shown in FIG. 7A is disclosed in Non-Patent Literature 1. Similarly, a study result to the effect that if a sample C in which a constant force was applied to the teeth and a sample D in which a constant force and a vibration force were applied to the teeth are compared, the sample D in which the constant force and vibration force were applied is more effective in shortening the period as shown in FIG. 7B is disclosed in non-Patent Literature 2.

According to these studies, the application of the vibration force to the teeth remarkably shortens the period of orthodontic treatment to about ½ to ⅓ as compared to conventional technologies. Further, it is sufficient to apply a vibration force only for 1.5 hours a day according to the former literature and only for 2 minutes at a time and once every two weeks according to the latter literature.

It can be understood from these studies that the teeth alignment by applying a vibration force as well as a constant force to the teeth is more effective in remarkably shortening the period of orthodontic treatment than the teeth alignment only by applying a constant force to the teeth using an orthodontic wire or the like.

Appliances for putting the above studies to practical use have been conventionally proposed. Specifically, Patent Literature 1 discloses an appliance provided with a dental mouthpiece to be mounted on teeth to urge movements of teeth to be aligned and means for applying ultrasonic vibration to tissues surrounding the mounted position of the dental mouthpiece. Further, Patent Literature 2 discloses an appliance for applying ultrasonic vibration to teeth to be aligned.

However, the appliances disclosed in the above Patent Literatures 1, 2 have a problem that ultrasonic vibration cannot be efficiently applied to the teeth to be aligned since both of them receive the application of ultrasonic vibration from the outside, for example, by pressing an ultrasonic head against the cheek skin. Further, since the respective appliances require an ultrasonic generator, there is also a problem that treatment cannot be continued unless a patient goes to a dental clinic equipped with these appliances.

[Non-Patent Literature 1] Shimizu: "Journal of Japan Orthodontic Society" 45, pp. 56-72, 1986

[Non-Patent Literature 2] Ohmae et al.: "Journal of Japan Orthodontic Society" 60(4), p. 201, 2001

[Patent Literature 1] Japanese Unexamined Patent Publication No. 2002-102255

[Patent Literature 2] Japanese Unexamined Patent Publication No. 2004-201895

DISCLOSURE OF THE INVENTION

In order to solve the above problems, an object of the present invention is to provide an orthodontic appliance capable of efficiently applying vibration to teeth to be aligned and enabling a treatment to be easily and safely continued even at home.

In order to accomplish the above object, an orthodontic appliance according to the present invention comprises a load applying mechanism and a vibration generating actuator. The load applying mechanism is mounted on teeth to apply a load for teeth alignment to a specified tooth in the teeth. The vibration generating actuator includes a contact portion that is inserted into a buccal cavity containing the teeth from the outside and can come into contact with a part of the load applying mechanism corresponding to the specified tooth or the specified tooth, and applies a vibration force from the contact portion to the specified tooth or the part of the load applying mechanism corresponding to the specified tooth. Accordingly, this vibration generating actuator can efficiently apply the vibration force to the specified tooth or the part of the load applying mechanism corresponding to the specified tooth, thereby remarkably shortening a period required for teeth alignment.

BEST MODES FOR EMBODYING THE INVENTION

Hereinafter, best modes for embodying the present invention are described in detail with reference to the accompanying drawings.

Figure 1:
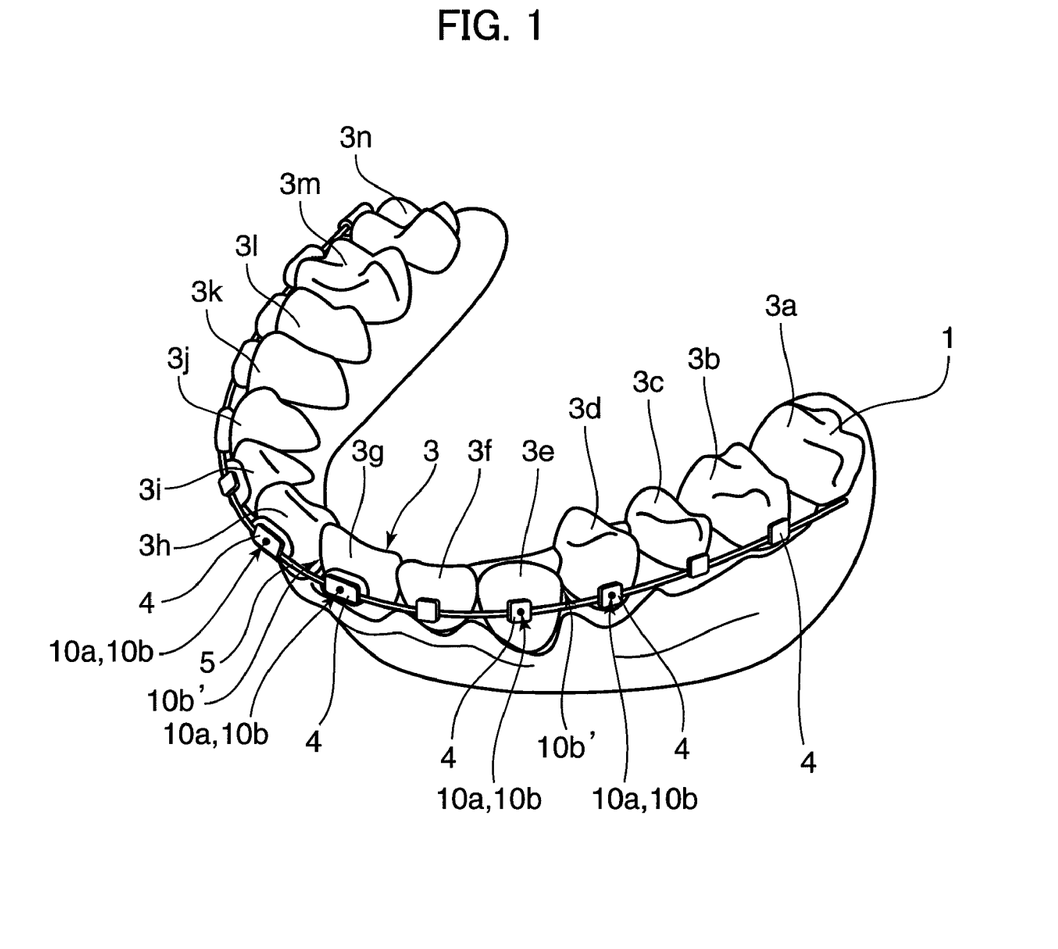
FIG. 1 is a perspective view of a dental cast of a lower dental arch where a mechanism including an orthodontic wire and brackets as a load applying mechanism according to a first embodiment of the invention is mounted on teeth.

FIG. 1 is a perspective view of a dental cast 1 of a lower dental arch according to a first embodiment of the present invention. This dental cast 1 has a teeth group 3 that includes a plurality of teeth 3a to 3n, wherein the teeth 3a, 3n are posterior teeth. A load applying mechanism for teeth alignment is mounted on the teeth 3b to 3m excluding these posterior teeth.

This load applying mechanism includes a plurality of brackets 4 to be fixed to the buccal surfaces of the teeth 3b to 3m and an orthodontic wire (arch wire) 5 arranged to connect these brackets 4. This orthodontic wire 5 is latched to the teeth 3b to 3m by the respective brackets 4. The orthodontic wire 5 is elastically deformably latched, so that an elastic restoring force thereof acts as a constant static load on the teeth group 3. The application of this static load corrects malocclusion. It should be noted that the load applying mechanism for aligning the teeth is not limited to the one shown in FIG. 1.

An orthodontic appliance according to this embodiment is provided with a vibration generating actuator 8 in addition to the above load applying mechanism. Examples of the vibration generating actuator 8 are shown in FIGS. 2A and 2B.

Figure 2A:
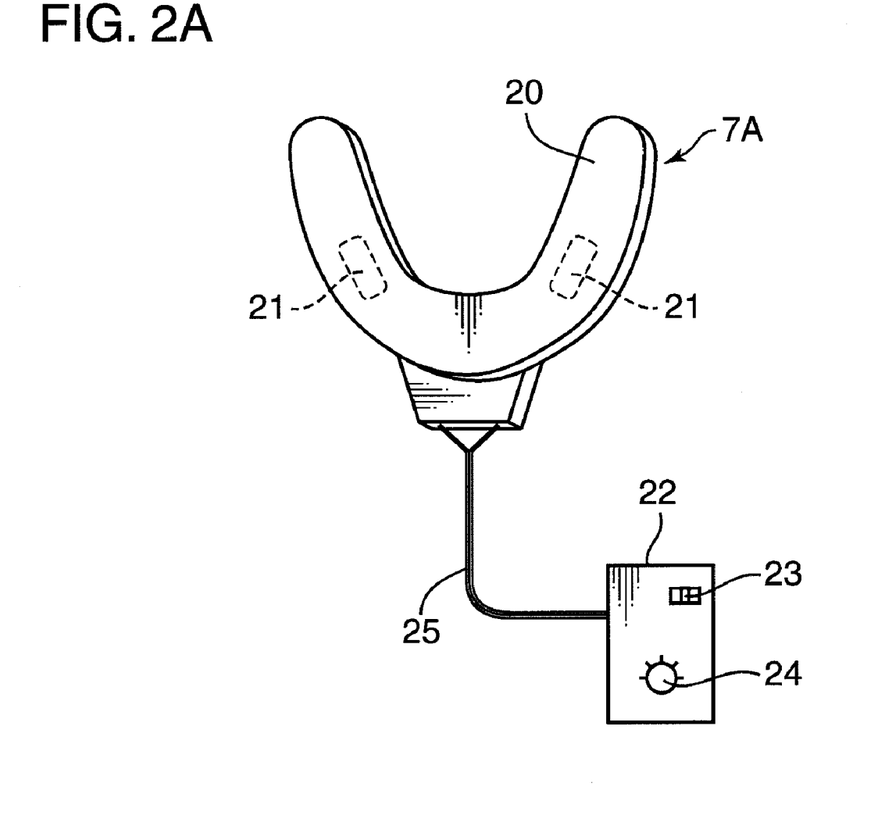
FIGS. 2A and 2B are perspective views showing examples of a vibration generating actuator.

FIG. 2A shows a bite board 7A as the vibration generating actuator. This bite board 7A includes a main body 20 to be chewed by the upper and lower teeth of a user (patient), vibrating elements 21 built in this main body 20, and a control box 22 electrically connected to the vibrating element 21s via cables 25. The vibrating elements 21 vibrate upon receiving the power supply and transmit this vibration to the teeth. The control box 22 has a switch 23 and a volume knob 24 and controls the frequency of the vibration generated by the vibrating elements 21 according to an operated amount of this volume knob 24.

The main body 20 of this bite board 7A is inserted into the buccal cavity from the outside, and brought into contact with the teeth 3d, 3e, 3g and 3h to be aligned, to which constant aligning forces are applied from the brackets 4 and the orthodontic wire 5, by being chewed by the upper and lower teeth. This contact enables the bite board 7A to efficiently apply vibration to the teeth 3d, 3e, 3g and 3h to be aligned. The application of such vibration remarkably shortens a period required for teeth alignment.

Figure 2B:
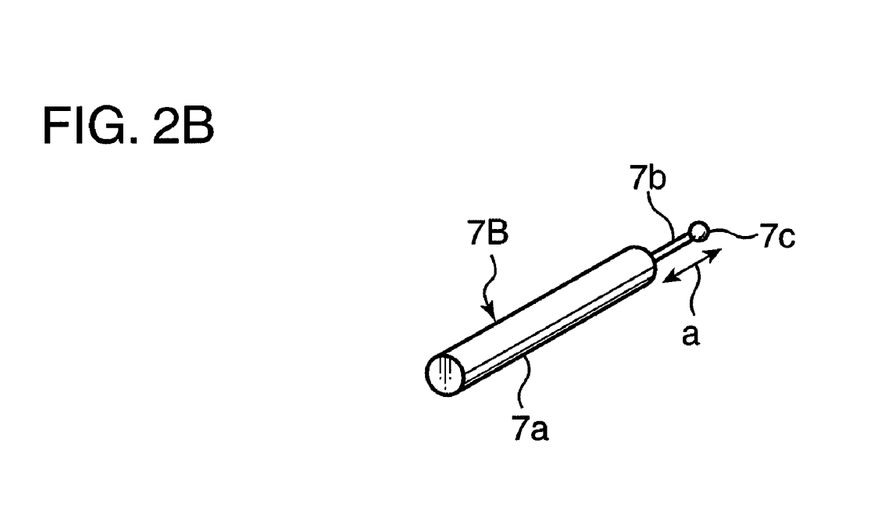

On the other hand, FIG. 2B shows a vibration generating probe 7B as the vibration generating actuator. This vibration generating probe 7B includes a main body 7a extending in one direction, a shaft 7b extending from this main body 7a along the central axis of the main body 7a, and a ball-shaped vibrating element 7c disposed at the tip of the shaft 7b, and the shaft 7b and the ball-shaped vibrating element 7c vibrate in axial directions (directions of arrows "a" in FIG. 2B) as power is supplied to the main body 20. For example, a vibration generating probe used in a vibration-type household electric toothbrush or electric shaver can be used as the vibration generating probe 7B.

In the above load applying mechanism, markings (colored markers) 10a are applied as positioning portions to the brackets 4 corresponding to specified teeth (e.g. teeth 3d, 3e, 3g and 3h to be aligned) of the teeth group 3 shown in FIG. 1. These markings 10a may be applied to the orthodontic wire 5 or markings may be applied to the teeth 3d, 3e, 3g and 3h to be aligned themselves.

The positioning portions according to the present invention are not limited to the markings 10a. For example, as shown in FIG. 1, dents 10b as the positioning portions may be formed in the specified brackets 4 constituting the load applying mechanism. Alternatively, a recess between the adjoining surfaces of the teeth 3d, 3e to be aligned and the one between the adjoining surfaces of the teeth 3g, 3h to be aligned shown in FIGS. 1 and 3C may constitute dents 10b' corresponding to the positioning portions.

Figure 3A:
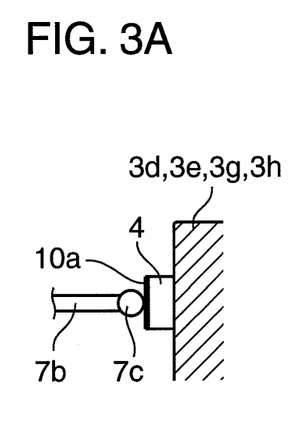
FIGS. 3A, 3B and 3C are sections showing contact states of the load applying mechanism and the vibration generating actuator.

Specifically, if the vibration generating probe 7B shown in FIG. 2B is used as the vibration generating actuator and the positioning portions of the load applying mechanism are the markings (colored markers) 10a shown in FIG. 3A, the ball-shaped vibrating element 7c of the vibration generating probe 7B is inserted into the buccal cavity from the outside, and brought into contact with the bracket 4 using the corresponding marking 10a as a marker. If the positioning portions are the dents 10b shown in FIG. 3B, the ball-shaped vibrating element 7c is brought into contact with the bracket 4 to fit into the corresponding dent 10b. If the positioning portions are the dents (recesses between the adjoining surfaces) 10b' shown in FIG. 3C, the ball-shaped vibrating element 7c is directly brought into contact with the teeth group 3 to fit into the dent 10b'.

Figure 3B:
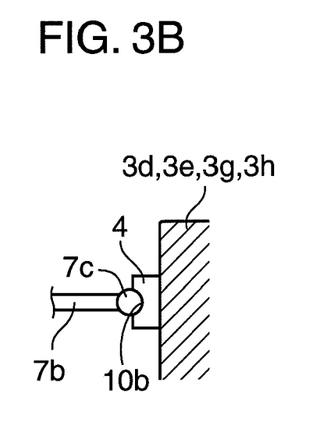
Figure 3C:
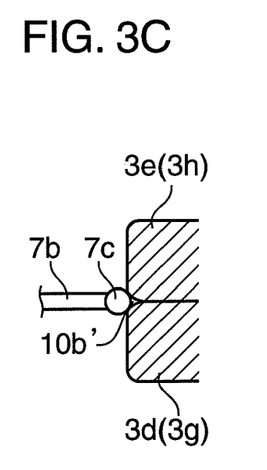

Any of the above contacts enables the vibration generating probe 7B to precisely apply vibration only to the teeth 3d, 3e, 3g and 3h to be aligned and their neighboring parts. Such application of the vibration remarkably shortens a period of orthodontic treatment.

Since the load applying mechanism, i.e. the mechanism for applying constant forces to the teeth 3d, 3e, 3g and 3h to be aligned is constructed by a plurality of brackets 4 and the orthodontic wire 5 connecting the brackets 4, it has a low cost.

The above positioning portions, i.e. the markings 10a provided on at least either the brackets 4 or the orthodontic wire 5, the dents 10b, and the dents 10b' formed by the recess between the adjoining surfaces of the teeth 3d, 3e to be aligned and the recess between the adjoining surfaces of the teeth 3g, 3h to be aligned serve as markers upon positioning the vibrating element 7c of the vibration generating probe 7B. Therefore, vibration can be more precisely applied to the teeth 3d, 3e, 3g and 3h to be aligned.

Specifically, the markings 10a as the positioning portions enable the position where the vibrating element 7c of the vibration generating probe 7B should come into contact to be precisely confirmed by the eyes.

Further, since the dents 10b, 10b' as the positioning portions have a function of guiding the vibrating element 7c, the vibrating element 7c and the load applying mechanism or the teeth can be more easily and precisely brought into contact with each other.

Figure 4:
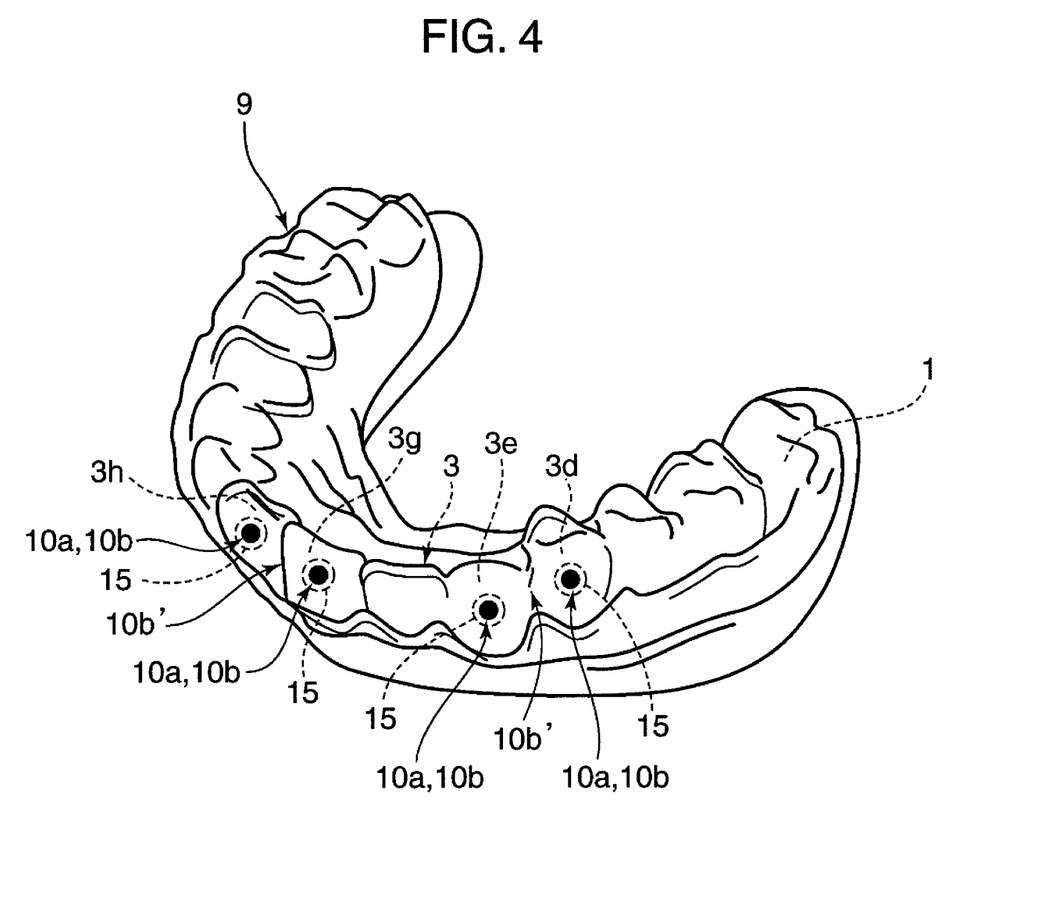
FIG. 4 is a perspective view of a dental cast of a lower dental arch where a dental mouthpiece as a load applying mechanism according to a second embodiment of the invention is mounted on teeth.
Figure 5A:
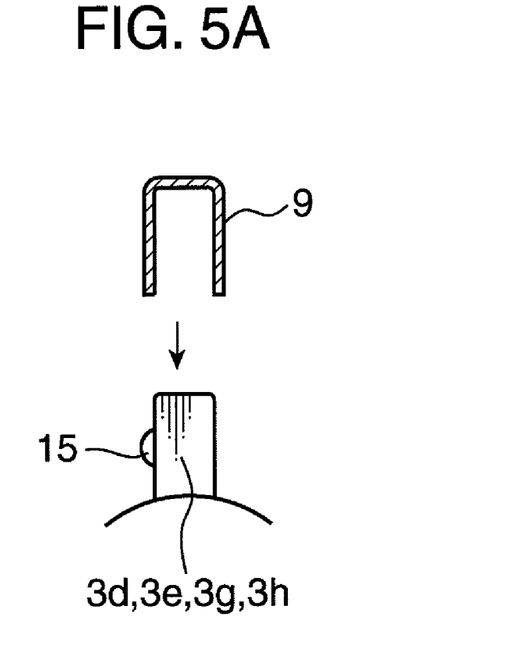
FIGS. 5A and 5B are partial side views in section showing a state before the dental mouthpiece is mounted on teeth and a state where the dental mouthpiece is mounted on the teeth, respectively.
Figure 5B:
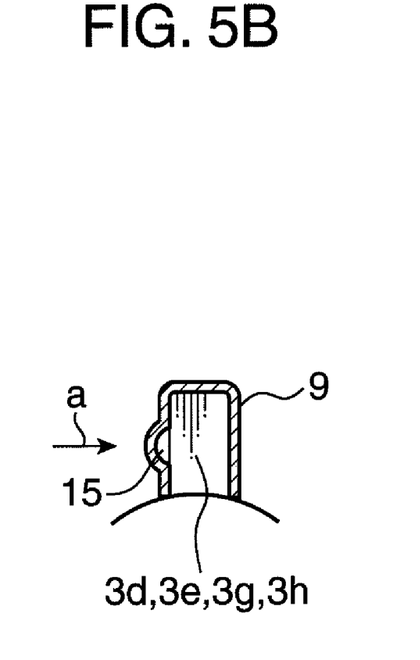

A second embodiment of the present invention is shown in FIGS. 4 and 5. A load applying mechanism according to this embodiment is constructed by a dental mouthpiece 9 and projections 15, and this load applying mechanism applies constant forces (static loads) to teeth 3d, 3e, 3g and 3h to be aligned.

As shown in FIG. 5A, each projection 15 is so fixed to the front surface of a corresponding one of the teeth 3d, 3e, 3g and 3h to be aligned of a teeth group 3 as to project forward. The dental mouthpiece 9 is fitted over these projections 15 as shown in FIGS. 4 and 5B, and forcibly mounted on the teeth group 3. This mounted dental mouthpiece 9 comes to possess contraction forces, which concentrate on the projections 15. The forces concentrated on the projections 15 are applied to the teeth 3d, 3e, 3g and 3h to be aligned as constant forces (arrow "a") for teeth alignment.

A material for ordinary mouthpieces (or mouth guards) and having guaranteed hygienic safety is normally used as the material of the dental mouthpiece 9. The dental mouthpiece 9 is preferably cast into a suitable shape using, for example, an EVA (ethylene vinyl acetate) sheet which is a polymer material. Such a material is preferable since having little side effects on teeth and gingival tissues such as allergy. The material of the dental mouthpiece 9 is suitably selected from soft materials, hard materials or admixtures of soft and hard materials depending on the degree of teeth alignment.

Markings (colored markers) 10a as positioning portions are applied to parts of the dental mouthpiece 9 corresponding to the teeth 3d, 3e, 3g and 3h to be aligned. The positioning portions are not limited to the markings 10a. For example, instead of the markings 10a, dents 10b shown in FIG. 6B may be formed in the outer surface of the dental mouthpiece 9. Alternatively, as shown in FIGS. 4 and 6C, dents 10b' formed in the outer surface of the dental mouthpiece 9 in correspondence with a recess between the adjoining surfaces of the teeth 3d, 3e to be aligned and a recess between the adjoining surfaces of the teeth 3g, 3h may be respectively used as the positioning portions.

Figure 6A:
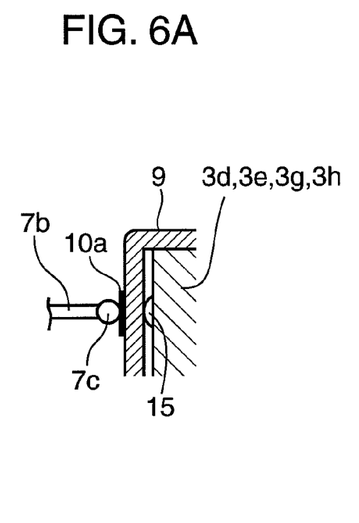
FIGS. 6A, 6B and 6C are sections showing contact states of the dental mouthpiece and a vibration generating actuator.

Similar to the first embodiment, if the ball-shaped vibrating element 7c of the vibration generating probe 7B is inserted into the buccal cavity and the markings (colored markers) 10a shown in FIG. 6A constitute the positioning portions, the ball-shaped vibrating element 7c is brought into contact with the marking 10a. If the dents 10b shown in FIG. 6B or the dents 10b' shown in FIG. 6C constitute the positioning portions, the ball-shaped vibrating element 7c is brought into contact with the dental mouthpiece 9 to fit into the dent.

Figure 6B:
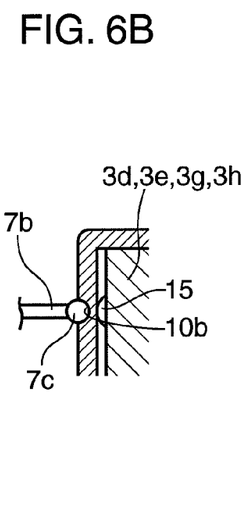
Figure 6C:
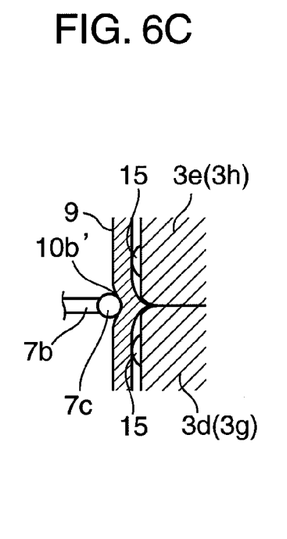

In any of the cases, the ball-shaped vibrating element 7c can be precisely brought into contact with the outer surfaces of parts of the dental mouthpiece 9 corresponding to the teeth 3d, 3e, 3g and 3h to be aligned. This can remarkably shorten a period of orthodontic treatment.

Also, in the case where the dental mouthpiece 9 is used, the bite board 7A shown in FIG. 2A can be used as the vibration generating actuator. In such a case, the main body 20 of the bite board 7A is chewed by the upper and lower teeth via the dental mouthpiece 9. In this way, the main body 20 can be brought into contact with the parts of the dental mouthpiece 9 corresponding to the teeth 3d, 3e, 3g and 3h to be aligned to which constant forces are applied. Thus, vibration can be efficiently applied to the teeth 3d, 3e, 3g and 3h to be aligned. This can remarkably shorten a period of orthodontic treatment.

The dental mouthpiece 9 is forcibly fitted on the teeth group 3 to be placed over the projections 15 fixed to the teeth 3d, 3e, 3g and 3h to be aligned, thereby applying constant forces to the teeth 3d, 3e, 3g and 3h to be aligned. Thus, as compared to the load applying mechanism including the brackets 4 and the orthodontic wire 5, the dental mouthpiece 9 can be easily mounted on and detached from the teeth group 3 to thereby reduce burdens on patients. Further, since the dental mouthpiece 9 shown in FIGS. 4 and 6A to 6C has the markings 10a or the dents 10b, 10b' that are the positioning portions as markers for the contact positions of the vibrating element 7c of the vibration generating probe 7B, vibration can be more precisely applied to the teeth 3d, 3e, 3g and 3h to be aligned.

The positioning portion is not limited to the above-mentioned positioning means for indicating a contact position of the vibrating element 7c to the load applying mechanism including the bracket 4 and the wire 5 or the load applying mechanism including the mouthpiece 9, but may be a positioning means for indicating a contact position of the vibrating element to the teeth. As a positioning portion, for example, it may be appreciated to provide a member extending upward or downward from an appropriate position of the wire 5 and having a shape pointing a contact position to which the vibrating element is to come into contact. Also, the positioning portion may be a through hole which is formed in the mouthpiece 9 and is operable to permit insertion of the vibrating element and guide the vibrating element to the suitable contact position of the teeth.

As described above, an orthodontic appliance according to the present invention comprises a load applying mechanism and a vibration generating actuator. The load applying mechanism is mounted on teeth to apply a load for teeth alignment to a specified tooth in the teeth. The vibration generating actuator includes a contact portion that is inserted into a buccal cavity containing the teeth from the outside and can come into contact with a part of the load applying mechanism corresponding to the specified tooth or the specified tooth, and efficiently applies a vibration force from the contact portion to the specified tooth or the part of the load applying mechanism. This can remarkably shorten a period required for teeth alignment.

The load applying mechanism preferably includes brackets to be fixed to the buccal surfaces of a plurality of teeth in the teeth and an orthodontic wire connecting the brackets, latched by the brackets while being elastically deformed and applying an elastic restoring force thereof to the specified tooth as the load. This mechanism has a simple construction and a low cost.

The load applying mechanism may include a projection fixed to the specified tooth in the teeth to project from the specified tooth and a dental mouthpiece to be mounted on the teeth over the projection, thereby applying a constant force to the tooth to which the projection is fixed. This dental mouthpiece can be easily mounted and detached, which reduces burdens on patients.

The vibration generating actuator preferably includes a main body chewable by upper and lower teeth and a vibrating element built in the main body to generate vibration. This vibration generating actuator can apply vibration to the specified tooth or a part of the load applying mechanism corresponding to the specified tooth only by the main body thereof being chewed by a patient.

The vibration generating actuator may include a vibrating element for generating vibration, and the vibrating element may be so shaped as to be able to come into contact with the part of the load applying mechanism corresponding to the specified tooth or the specified tooth. This vibrating element can efficiently apply vibration to the specified tooth.

The load applying mechanism more preferably includes a positioning portion for determining a position where the vibrating element is supposed to come into contact with the load applying mechanism. This positioning portion helps the vibrating element to more precisely come into contact with the load applying mechanism or a suitable position of the teeth.

The positioning portion is preferably a marking indicating the contact position of the vibrating element or a dent having such a shape that the vibrating element can be fitted into. The latter, i.e. the dent has a function of guiding the vibrating element to the suitable contact position.

What is claimed is:

1. An orthodontic appliance for correcting malocclusion, comprising:
   a load applying mechanism mountable on teeth contained in a buccal cavity to apply a load for malocclusion correction to a specified tooth in the teeth, and
   a vibration generating actuator comprising a vibration generation probe having a shaft and a vibrating element with a spherical surface, the shaft including a tip which is at a distal end of the shaft and oriented in an axial direction of the shaft, the vibrating element being positioned at the tip of the shaft, and wherein the spherical surface of the vibrating element is configured to be inserted into the buccal cavity followed by the shaft so as to contact a part of the load applying mechanism corresponding to the specified tooth in the teeth to apply a vibration force from the vibrating element to the tooth or the part of the load applying mechanism, and wherein the load applying mechanism comprises a positioning portion which comprises a recess having a shape corresponding to a shape of the spherical surface of the vibrating element such that the vibrating element is received in the recess in a direction transverse to a side wall surface of the tooth to determine a position at which the vibrating element of the vibration generation probe inserted into the buccal cavity from the outside thereof contacts the load applying mechanism.

2. The orthodontic appliance according to claim 1, wherein the load applying mechanism includes brackets to be respectively fixed to the buccal surfaces of a plurality of teeth in the teeth contained in the buccal cavity, and an orthodontic wire connecting the brackets, latched by the brackets while being elastically deformed and applying an elastic restoring force thereof as a load on the specified tooth; and the positioning portion is applied to a specified bracket among said brackets, the specified bracket corresponding to the specified tooth.

3. The orthodontic appliance according to claim 1, wherein the load applying mechanism includes a projection to be fixed to the specified tooth in the teeth to project from the specified tooth contained in the buccal cavity, and a dental mouthpiece to be mounted on the teeth over the projection, thereby applying a constant force to the tooth to which the projection is fixed.

4. The orthodontic appliance according to claim 1, wherein the vibrating element comprises a ball-shaped vibrating element.

5. An orthodontic appliance for correcting malocclusion, comprising:

a load applying mechanism mountable on teeth contained in a buccal cavity to apply a load for malocclusion correction to a specified tooth in the teeth, and a vibration generating actuator comprising a vibration generation probe having a shaft including a tip at a distal end of the shaft and oriented in an axial direction of the shaft, and the tip having a predetermined shape, wherein the predetermined shape of the tip of the shaft is configured to be inserted into the buccal cavity followed by the shaft so as to contact a part of the load applying mechanism corresponding to the specified tooth in the teeth to apply a vibration force generated by the shaft to the tooth or the part of the load applying mechanism, and wherein the load applying mechanism comprises a positioning portion which comprises a recess having a shape corresponding to the predetermined shape of the tip of the shaft such that the predetermined shape is received in the recess to determine a position at which the vibration generation probe inserted into the buccal cavity from the outside thereof contacts the load applying mechanism, the recess being positioned at a facial surface of the specified tooth, wherein the predetermined shape is arcuate.

6. The orthodontic appliance according to claim 5, wherein the load applying mechanism includes brackets to be respectively fixed to the buccal surfaces of a plurality of teeth in the teeth contained in the buccal cavity, and an orthodontic wire connecting the brackets, latched by the brackets while being elastically deformed and applying an elastic restoring force thereof as a load on the specified tooth; and the positioning portion is applied to a specified bracket among said brackets, the specified bracket corresponding to the specified tooth.

7. The orthodontic appliance according to claim 5, wherein the load applying mechanism includes a projection to be fixed to the specified tooth in the teeth, to project from the specified tooth contained in the buccal cavity, and a dental mouthpiece to be mounted on the teeth over the projection, thereby applying a constant force to the tooth to which the projection is fixed.

8. The orthodontic appliance according to claim 5, wherein the predetermined arcuate shape is spherical.

9. The orthodontic appliance according to claim 5, wherein the predetermined arcuate shape is defined by a surface of a ball-shaped vibrating element.

* * * * *